United States Patent [19]

Yoshikawa et al.

[11] 4,344,327
[45] Aug. 17, 1982

[54] ELECTRONIC SCANNING ULTRASONIC DIAGNOSTIC SYSTEM

[75] Inventors: Yoshihiro Yoshikawa; Takao Katabami; Katsumi Fujinaga; Yoshiaki Kobayashi, all of Mitaka, Japan

[73] Assignee: Aloka Co., Ltd., Tokyo, Japan

[21] Appl. No.: 219,578

[22] Filed: Dec. 23, 1980

[30] Foreign Application Priority Data

Dec. 28, 1979 [JP] Japan .................................. 54-170408
Dec. 28, 1979 [JP] Japan .................................. 54-170409

[51] Int. Cl.³ ...................... G01N 29/04; A61B 10/00
[52] U.S. Cl. ........................................ 73/626; 128/661
[58] Field of Search .................................. 73/618–621, 73/625, 626; 128/660, 661

[56] References Cited

U.S. PATENT DOCUMENTS 3,817,089 6/1974 Eggleton et al. ................ 73/625 X
3,938,502 2/1976 Bom .................................. 128/661 X Primary Examiner—James J. Gill
Attorney, Agent, or Firm—Koda and Androlia

[57] ABSTRACT

An electronic scanning ultrasonic diagnostic system comprising a probe having ultrasonic beam emitting surface, in which plural ultrasonic wave transducers are convexly arranged at equal distances, emitting desired sector scanning ultrasonic beams, a transmitting and receiving wave control circuit dividing transducers into optional and plural groups and repeatedly performing of transmitting and receiving action with ultrasonic directivities respectively different to each group, and supplying ultrasonic beam scanning signals to an image display section with an assumption that the respective extension lines of each sector scanning ultrasonic beams coincide with the center of the arc shape of the probe.

3 Claims, 7 Drawing Figures

ELECTRONIC SCANNING ULTRASONIC DIAGNOSTIC SYSTEM

BACKGROUND OF THE INVENTION

1. Field of the Invention

The present invention relates to an electronic scanning ultrasonic diagnostic system and more particularly to an electronic scanning ultrasonic diagnostic system which emits sector scanning ultrasonic beams.

2. Prior Art

It is well known to observe a human body for medical treatment by ultrasonic diagnostic equipment which emits ultrasonic beams into the human body to be examined and receives echoes reflected from tissues in the body. Scanning of the ultrasonic beam along the desired section can display B-scope image and provide various diagnosis information promptly. As for the scanning method of the above mentioned ultrasonic beams, there is a method of manual or mechanical handling of a probe which emits ultrasonic beams, and there is another way of high speed scanning method in which the probe is fixed and ultrasonic transducers arranged in a row in the probe is electronically controlled. The latter electronic scanning type probe are widely utilized, since it acts rapidly and allows real-time images of dynamic tissue motion to be observed. The electronic scanning type probe is ordinarily classified into linear scanning method and a sector scanning method. In order to observe internal tissues which occupy relatively most of the body, preferred is the sector scanning method in the latter. In the case observing a heart in motion at real-time particularly, it requires 10 cm in effective observing length, and preferred is the probe in the sector scanning method which provides sector ultrasonic beams emitted from small ultrasonic beam emitting surface in wide emitting angle, since utilization of the probe in such length in the conventional linear scanning method hardly produces clear tomograms, being affected by images of ribs or the like.

In FIG. 1, shown therein is a conventional sector electronic scanning type probe. The probe 12 attached to a human body 10 emits ultrasonic beams 200 into the body 10 at a predetermined emitting angle 100. According to the sector electronic scanning type probe described in FIG. 1, the ultrasonic beams 200 can be emitted towards the heart between the adjacent ribs and can display a considerably wide area of the tissue producing a clear image, accordingly.

In the prior art device in FIG. 1, however, there are such drawbacks that the circuit composition is extremely complicated for the achievement of accurate delay control at the plural ultrasonic wave transducers built in the probe 12 at every timing of emitting and receiving the ultrasonic waves in order to obtain the sector scanning ultrasonic beams 200. In the conventional electronic scanning probe, there exists interference among ultrasonic wave signals emitted from each of the ultrasonic wave transducers having respective different delay times, and unnecessary artificial echoes having different directivities are produced. The ultrasonic wave transducers must be arranged in a row at shorter distances or the exciting frequency of the ultrasonic waves must be lowered so that the unnecessary artificial echoes can be less produced, which is another drawback limiting the resolution of reflected echoes. Furthermore, in the prior art device illustrated in FIG. 1, in the vicinity of the beam emitting surface there exists an area 300 drawn with oblique lines which is unable to be observed since the origin of the coordinate axis of the emitting angle 100 is determined in the center of the beam emitting surface of probe 12.

For the other improved conventional sector electronic scanning type probe, a concave probe is introduced as shown in FIG. 2. This prior art device can provide the sector ultrasonic beams 200 by means of simple control circuit without supplying respectively different delay times to each of the ultrasonic wave transducers as described in FIG. 1, since the ultrasonic waves transducers are concavely arranged at equal distances. In the prior art device, however, a concave beam emitting surface 12a of the probe 12 does not contact the surface of the body 10 to inevitably make a gap between the both, which causes the remarkable attenuation of the ultrasonic beams, and a contact spacer 14 consisting of medium well passing ultrasonic waves must be installed on the beam emitting surface 12a as illustrated in FIG. 2. The contact spacer 14 has an advantage that an intersection 200a of ultrasonic beams 200 can be established in the vicinity of the surface of the body 10 as well as the gap between the beam emitting surface 12a of probe 12 and the surface of the body is buried. However, in this prior art device, the particular contact spacer makes the equipment complicated and less operational. Furthermore, the contact spacer 14 shown in FIG. 2 causes drawbacks such that there exists the attenuation of ultrasonic waves in its inside and the attenuating action decreases the echoe receiving sensitivity.

SUMMARY OF THE INVENTION

Accordingly, it is the general object of the present invention to provide an electronic scanning ultrasonic diagnostic system with a simple construction in which accurate images with high resolution can be attained by ultrasonic waves.

It is another object of the present invention to provide ultrasonic wave transmitting and receiving equipment having high resolution with a simple construction.

In keeping with the principles of the present invention the objects are accomplished with a probe having plural ultrasonic wave transducers selected out of the plural ultrasonic wave transducers in accordance with a predetermined program, at every timing of transmitting and receiving the ultrasonic waves and are characterized in that desired sector scanning ultrasonic beams are directly emitted into the body from the probe.

In accordance with this invention, the emitting surface of the probe is shaped in convexity to be contacted and buried in the surface of the body to be examined so that there exists no gap which would cause attenuation of ultrasonic waves between the emitting surface and the body. Accordingly, reflected echoes can be obtained with extremely high resolution.

In accordance with this invention, the object is further accomplished with a probe having plural ultrasonic wave transducers arranged in an arc shape at equal distances and emitting sector scanning ultrasonic beams into the body to be examined, and a transmitting and receiving ultrasonic wave control circuit dividing the above mentioned ultrasonic wave transducers into plural groups optionally combining two or more transducers and repeatedly performing of ultrasonic beam transmitting and receiving action with ultrasonic beam directivities respectively different to each group, and is characterized in that simple control action can emit uniform ultrasonic beams with dense interval to provide an accurate image with high resolution.

In accordance with this invention, the transmitting and receiving ultrasonic wave control circuit can remarkably simplify a scanning control of the image display section by means of supplying received ultrasonic beam signals to the image display section with such an assumption that the beam extension lines of each sector scanning ultrasonic beam coincide with the center of the arc of the probe.

BRIEF DESCRIPTION OF THE DRAWINGS

The above mentioned and other features and objects of the present invention will become more apparent by reference to the following description taken in conjunction with the accompanying drawings, wherein like reference numerals denote like elements and in which.

DESCRIPTION OF THE INVENTION

Figure 3:
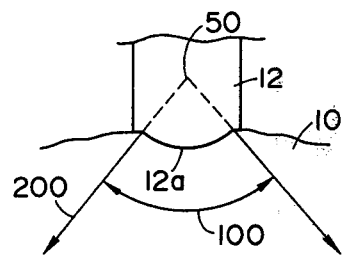
FIG. 3 is an illustration showing an emitting state of the ultrasonic waves in a preferred embodiment of the probe utilized in an electronic scanning ultrasonic diagnostic system in accordance with the teachings of the present invention.

In FIG. 3, shown therein is the appearance of a probe of the electronic scanning ultrasonic diagnostic system in accordance with the teachings of the present invention. A convex ultrasonic beam emitting surface 12a of a probe 12, contacts pressurized to the surface of a body 10 to be examined and whole area of the emitting surface 12a, is buried in the body 10. Accordingly, ultrasonic beams 200 emitted from the probe 12 are directly emitted into the body 10 and an accurate display image can be obtained without accompanying attenuating action.

Figure 4:
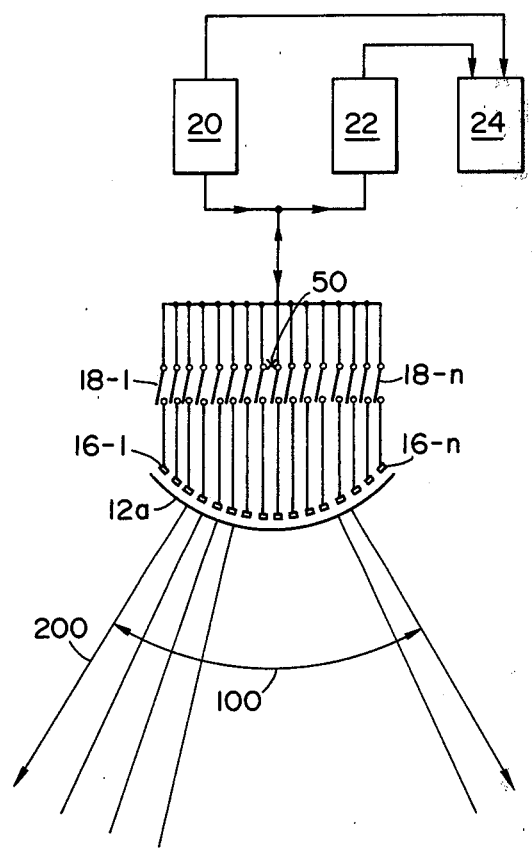
FIG. 4 is an illustration showing an internal composition of the probe shown in FIG. 3 and an energizing means of the ultrasonic wave transducers.

In FIG. 4, shown therein is an internal composition of the probe and means of driving ultrasonic wave transducers in accordance with the teachings of the present invention. In the inner part of the probe convexly arranged are the plural ultrasonic wave transducers 16-1~16-n at equal distances along the emitting surface 12a. In FIG. 4, each of the transducers 16 consists of an electric sound converter such as PZT, etc. and comprises rectangualr emitting surface.

Connected to each of the transducers 16, is an analog switch 18-1~18-n, which switches the connection of selected transducer to a transmitter 20 and a receiver 22.

Reflected echoe signals to the receiver 22 are supplied to an image display monitor 24 consisting of a CRT, etc. and displayed on the image display monitor 24 which is under scanning control by synchronous control signals from the transmitter 20.

As described in the above, the ultrasonic diagnostic system is composed in accordance with the teachings of the present invention, and in the following is described its operation.

The optionally selected numbers and combinations of ultrasonic wave transducers from ultrasonic wave transducer group 16 by analog switch group 18 which is controlled on and off according to a predetermined program are driven at every transmitting timing of the transmitter 20. In the illustrated embodiment, each of the ultrasonic wave transducer groups 16 consisted of combinations of adjacent four transducers is energized to drive from the left at every timing of transmitting and receiving the signals, and the combinations in the ultrasonic wave transducers are selected toward right one after another to be driven. In other words, the first transmitting and receiving waves are emitted by the combination in the ultrasonic waves transducers group 16-2 16-5. Accordingly, the ultrasonic beams 200 are radiated from the probe toward the directions of normal lines of the emitting surface 12a by supplying the simultaneous energizing signals from the transmitter 20 to each of selected untrasonic wave transducers without any delay control required, and ultrasonic beams 200 can perform sector scanning at an emitting angle 100 which centers the center point 50 of the arc of the probe.

As described in the above, in accordance with the present invention the ultrasonic beams can be radiated from the emitting surface of the probe into the body to be examined at a desired emitting angle. In observing a heart, for example, close contact of the probe between two adjacent ribs enables sector scanning ultrasonic beams to be emitted into the body in extremely good conditions. In accordance with the present invention, the supply of simultaneous energizing signals without any delay control to each of the ultrasonic wave transducers does not produce such unnecessary artificial echoes that accurate image with high resolution can be obtained along with the increased energizing frequency, and an electronic circuit to drive the ultrasonic wave transducers can be remarkably simplified since the delay control is not required.

Furthermore, in accordance with the ultrasonic diagnostic system of the present invention, there is no gap existing between the probe and the body to be examined, since the convex emitting surface of the probe contact is pressurized to the body, and there is no media required such as the conventional contact spacer, etc., which enables the system to be simplified and the suppression of the ultrasonic waves caused from the intermediate medium material to be firmly removed. In accordance with the present invention, simple contact of the probe to the tissue taken out during operation could perform rapid observation of the inside of the tissue and it is preferable as the ultrasonic diagnostic system to be used during an operation.

Figure 1:
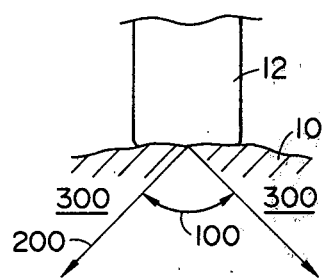
FIG. 1 is an illustration showing an emitting condition of the ultrasonic beams of a sector electronic scanning type probe using a conventional delay control.
Figure 2:
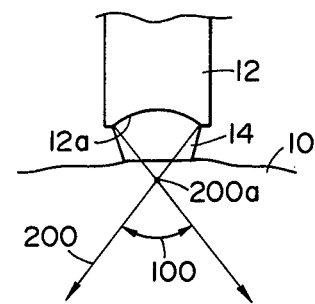
FIG. 2 is an illustration showing an emitting condition of the ultrasonic beams in an electronic scanning type probe using conventional concave emitting surface.

As described heretofore, in accordance with the present invention sector ultrasonic beams 200 can be obtained by the simple control circuit since the ultrasonic wave transducers 16-1~16-n are convexly arranged at equal distances and every different delay time shown in FIG. 1 is not required to be given to every ultrasonic wave transducer.

In the arc shaped probe, however, each ultrasonic beam is all directed to the normal line of the arc, and the distance between the beams become comparatively wider. At the end portion of the sector scanning ultrasonic beams is remarkably enlarged the distance between the beams, and the resolution at this portion is decreased in accuracy.

Figure 5:
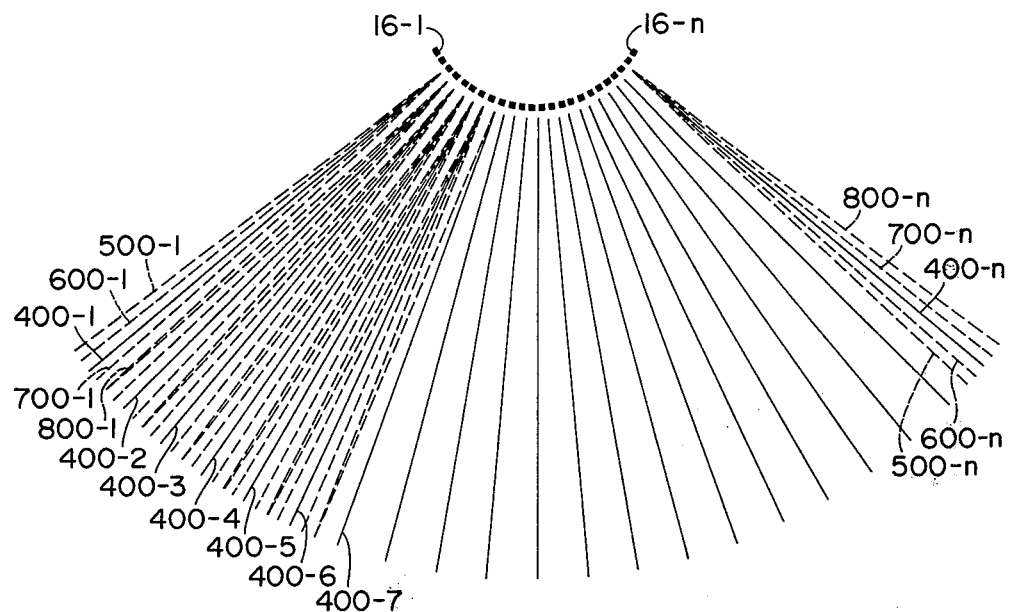
FIG. 5 is an illustration showing a convex probe preferred in the transmitting and receiving equipment of ultrasonic waves, and ultrasonic beams in accordance with the teachings of the present invention.
Figure 7:
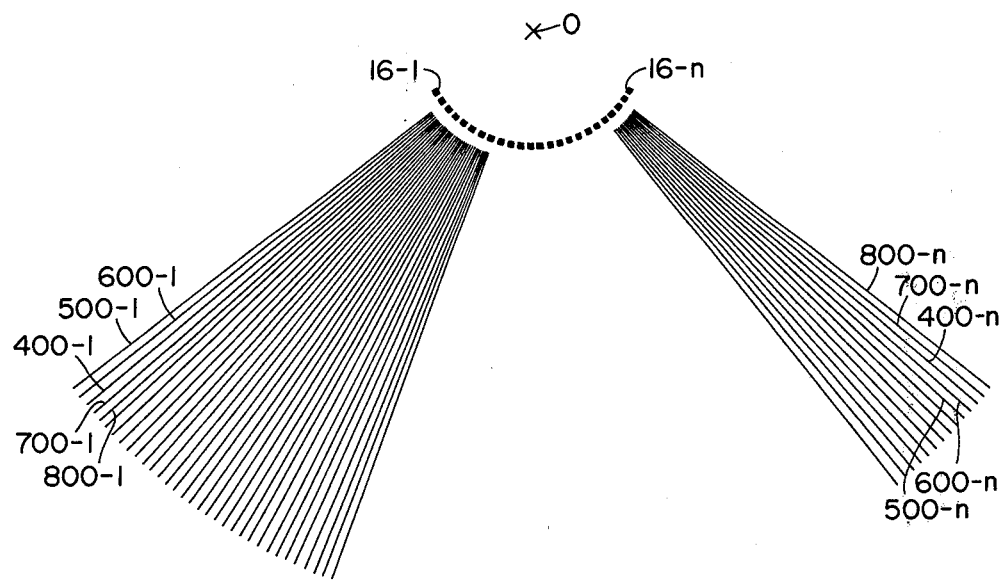
FIG. 7 is an illustration showing hypothetical ultrasonic beams, one example of image display action preferred in the present invention.
Figure 6:
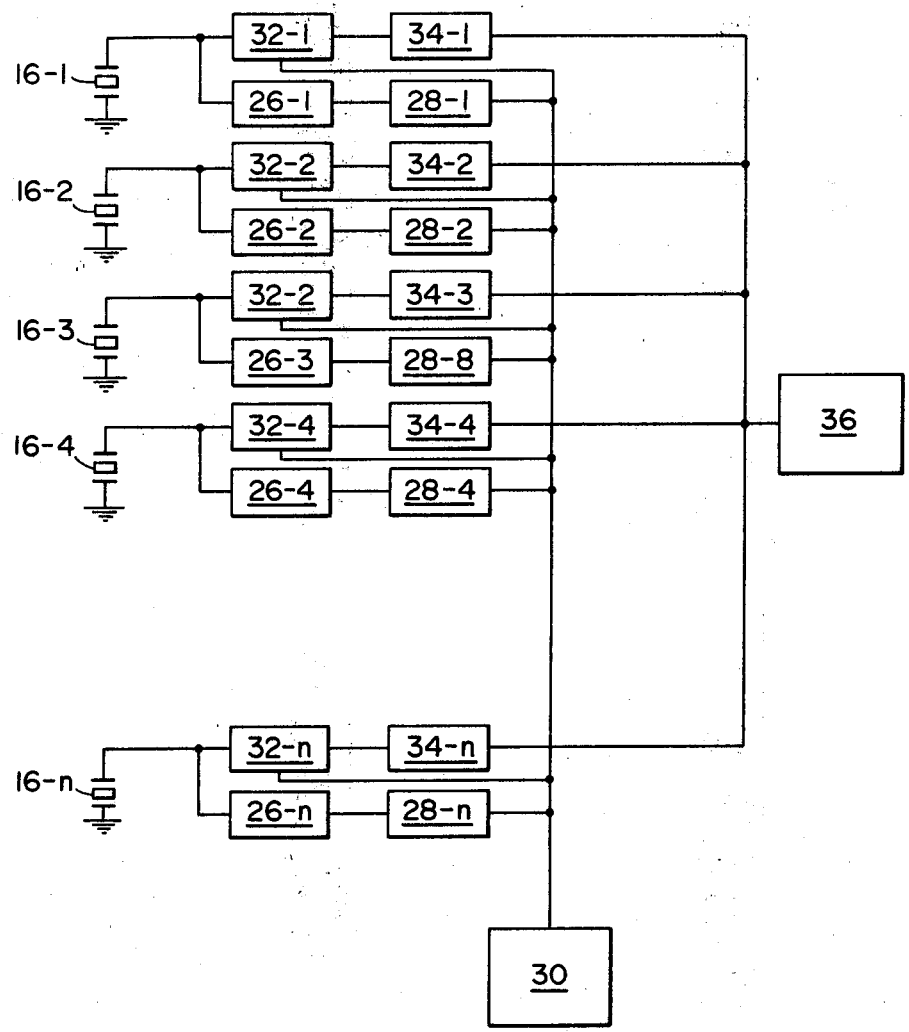
FIG. 6 is a block diagram showing a preferred embodiment of a control circuit of the transmitting and receiving ultrasonic wave preferred in FIG. 5.

In order to improve the resolution mentioned above, the present invention offers a novel ultrasonic beam transmitting and receiving system, and a preferred embodiment of the system is described hereafter, referring to FIGS. 5 through 7.

In FIG. 5, shown therein is the probe having plural ultrasonic wave transducers which are convexly arranged, and its ultrasonic beams. In FIG. 6, shown therein is an embodiment of transmitting and receiving wave control circuit which makes the probe shown in FIG. 5 perform transmitting and receiving action of the ultrasonic beams in accordance with the teachings of the present invention.

As evident from FIG. 5, rectangular ultrasonic wave transducers 16-1~16-n consisting of electric sound converters such as PZT, etc. are convexly arranged at equal distance in the probe. The transmitting and receiving action of ultrasonic beams is controlled by the transmitting and receiving wave control circuit illustrated in FIG. 6, and transmitting signal from each of the transmitting circuits 26-1~26-n is supplied to each of the ultrasonic waves transducers 16-1~16-n. Each of the delay trigger circuits 28-1~28-n is connected to each of the transmitting circuits 26-1~26-n, and each of the delay trigger circuits 28-1~28-n is individually controlled by a control circuit 30 at an individual predetermined delay time. The transmitting system of the transmitting and receiving wave control circuit is composed as mentioned in the above, and the transmitting signal having the predetermined delay time is supplied to any ultrasonic wave transducer 16 selected by the control circuit 30.

On the other hand, in order to perform a receiving action of reflected echoes received by the ultrasonic wave transducers 16, each of the receiving wave switching circuits 32-1~32-n is connected to each of the ultrasonic wave transducers 16-1~16-n and receiving action of the receiving wave switching circuits 32-1~32-n is controlled by the controlling signal from the above mentioned circuit 30. Each of the delay circuits 34-1~34-n is coupled with each of the receiving wave switching circuits 32-1~32-n, and the output from each of the delay circuits 34-1~34-n is supplied as receiving signals to an image display section, which is not illustrated by way of a receiving circuit 36.

Two or more ultrasonic wave transducers among the above mentioned ultrasonic wave transducers 16 are optionally combined into plural groups by the transmitting and receiving wave control circuit shown in FIG. 6. In the illustrated embodiment, four individual ultrasonic wave transducers 16 are combined into one group. Each one of the ultrasonic wave transducer groups receives plural ultrasonic beams having different ultrasonic beam directivities at every timing of transmitting and receiving ultrasonic beams.

Referring to the ultrasonic beams in FIG. 5, the transmitting and receiving wave action is described hereinafter in accordance with the teachings of the present invention.

In the illustrated embodiment, each group composed of four ultrasonic wave transducers 16 performs ultrasonic beam transmitting and receiving action five times each. The ultrasonic beams 400-1~400-n illustrated by the solid lines in FIG. 5 show basic ultrasonic beams directed toward the direction of normal lines of an arc formed by the ultrasonic wave transducers 16-1~16-n, and the basic ultrasonic beams are provided by the supply of simultaneous transmitting signals having no delay time one other, to each group composed of four ultrasonic wave transducers 16. The first basic ultrasonic beam 400-1 is provided by the supply of the same transmitting signals to the ultrasonic wave transducers 16-1~16-4, and the basic ultrasonic beam 400-2 is provided by the supply of the same transmitting signals to the ultrasonic wave transducers 16-2~16-5.

The present invention has such characteristics that every radiation of the basis ultrasonic beam accompanies at least one supplementary ultrasonic beam emitting.

In the illustrated embodiment, four supplementary ultrasonic beams 500, 600, 700 and 800 are emitted together with each of the ultrasonic beams 400. The basic ultrasonic beams 400 and each of the supplementary ultrasonic beams 500, 600, 700 and 800 have respectively different ultrasonic beam directivities. At the delay trigger circuits 28 the different delay times are provided to four ultrasonic wave transducers selected by the control circuit 30 illustrated in FIG. 6 at every timing of transmitting and receiving waves so that the supplementary ultrasonic beams having the above mentioned different ultrasonic beam directivities are obtained. Taking the example of basic ultrasonic beam 400-1, the supplementary ultrasonic beam 500-1 illustrated at the clockwise side of the basic ultrasonic beam 400-1 is obtained when the ultrasonic wave transducers 16-1~16-4 are providing the transmitting signals having the delay times increasing in the order of transducers 16-4, 16-3, 16-2 and 16-1, and the supplementary ultrasonic beam 600-1 is obtained when the transmitting signals are provided in shorter delay time. On the other hand, the supplementary ultrasonic beam 800-1 illustrated at the counter-clockwise side of the basic ultrasonic beam 400-1 is obtained when the ultrasonic wave transducers 16-1~16-4 are providing the transmitting signals having the delay time increasing in the order of transducers 16-1, 16-2, 16-3 and 16-4, and the supplementary ultrasonic beam 700-1 is obtained when the transmitting signals are provided in shorter delay time.

As mentioned in the above, the reflected echoes having extremely high resolution can be obtained with the equal radiation of dense ultrasonic beams to the sector scanning surface by the composition of four supplementary ultrasonic beams 500, 600, 700 and 800 at every basic ultrasonic beam 400 as shown by the dotted lines in FIG. 5. The reflected echoes are supplied to the receiving circuit 36 by way of the receiving wave switching circuit 32 selected by the control circuit 30 and the delay circuit 34 for converting receiving signals which are supplied to the image display section which is not illustrated. The delay times from the above mentioned delay circuits 34 are respectively determined in the same corresponding to the delay times in transmitting. The receiving properties can be set toward the ultrasonic beam direction shown in FIG. 5.

As described in the above, the first group of ultrasonic wave transducers 16-1 16-4 performs five times of the transmitting and receiving wave action with different ultrasonic directivities. After the ultrasonic beams 500-1, 600-1, 400-1, 700-1 and 800-1 are scanned, the second group of ultrasonic wave transducers 16-2~16-5 is selected by the control circuit 30 and the transmitting and receiving wave action of the ultrasonic beams having the different directivities is performed in the same order as the first group.

As evident from FIG. 5, the transmitting and receiving wave action of the ultrasonic beams can be performed with the five times higher density than the basic ultrasonic beams, and obtains an accurate image with extremely high resolution.

The receiving circuit 36 and the image display section to be connected to this circuit, which are not illustrated, can be composed of a display screen such as CRT, etc. The scanning action at the display screen such as CRT, etc. The scanning action at the display section can form accurate real-time image by the conformation to the ultrasonic beam emitting properties illustrated in FIG. 5, but the complicated scanning control action is required to form ultrasoinc beam focus on the image display section as shown in FIG. 5. In order to simplify the image display section it is preferable to display by the hypothetical ultrasonic beam receiving signals are processed with the assumption that each of the extension lines of the supplementary ultrasonic beams 500, 600, 700 and 800 in FIG. 5 coincides with the center 0 of the arc of the probe. According to the processing in FIG. 7, there exists some differences between the tissues and the image display, but it is preferable to enable the ultrasonic diagnostic system in a simple composition by the remarkable simplification in the control circuit.

In the illustrated embodiment, each group of selected ultrasonic wave transducers performs five times of the ultrasonic beam transmitting and receiving action, which can be determined at option to make the desired resolution. Also the scanning orders of the ultrasonic beams can be determined at option. For example, after all the basic ultrasonic beams are firstly scanned, the supplementary ultrasonic beams can be scanned in the orders.

Incidentally, the convex probe is described in the above embodiment, but it is also possible to obtain the same action of transmitting the receiving ultrasonic beam in the concave probe.

As described heretofore, the sector scanning image display with high density can be obtained with a few members of the ultrasonic wave transducers, and the energizing circuit of ultrasonic wave transducers can be remarkably simplified in comparison with the electronic scanning system in the prior art.

We claim:

1. An electronic scanning ultrasonic diagnostic system comprising:
  a probe havng ultrasonic beam emitting surface which is pressed to contact the surface of a body to be examined and in which plural ultrasonic wave transducers are convexly arranged at equal distances, said probe emitting desired sector scanning ultrasonic beams into the body without intermediate medium material; and
  means for energizing to drive selected ultrasonic wave trasducers out of said plural ultrasonic wave transducers according to the predetermined program at every timing of transmitting and receiving waves.

2. The electronic scanning ultrasonic diagnostic system according to claim 1, wherein said probe comprises plural ultrasonic wave transducers arranged in an arc shape at equal distances, and a transmitting and receiving wave control circuit dividing said ultrasonic wave transducers into plural groups optionally combining two or more transducers and repeatedly performing of ultrasonic beams transmitting and receiving action with ultrasonic directivities respectively different to each group.

3. The electronic scanning ultrasonic diagnositc system according to claim 2, wherein said transmitting and receiving wave control circuit supplies received ultrasonic beams signals to an image display section with such an assumption that the respective beam extension lines of each sector scanning ultrasonic beams coincide with the center of the arc shape of the probe.

* * * * *

REEXAMINATION CERTIFICATE (2286th)
United States Patent [19]
Yoshikawa et al.

[11] B1 4,344,327
[45] Certificate Issued  May 3, 1994

[54] ELECTRONIC SCANNING ULTRASONIC DIAGNOSTIC SYSTEM

[75] Inventors: Yoshihiro Yoshikawa; Takao Katabami; Katsumi Fujinaga; Yoshiaki Kobayashi, all of Mitaka, Japan

[73] Assignee: Aloka Co. Ltd., Tokyo, Japan

Reexamination Request:
No. 90/002,313, Apr. 2, 1991

Reexamination Certificate for:
Patent No.: 4,344,327
Issued: Aug. 17, 1982
Appl. No.: 219,578
Filed: Dec. 23, 1980

[30] Foreign Application Priority Data

Dec. 28, 1979 [JP] Japan ............... 54-170408
Dec. 28, 1979 [JP] Japan ............... 54-170409

[51] Int. Cl.⁵ ............... G01N 29/04; A61B 8/14
[52] U.S. Cl. ............... 73/626; 128/661.01
[58] Field of Search ............... 73/626, 625; 128/661.01

[56] References Cited
U.S. PATENT DOCUMENTS 3,817,089 6/1974 Eggleton et al. ............... 73/625
3,938,502 2/1976 Bom ............... 73/626
4,409,982 10/1983 Plesset et al. ............... 73/626

FOREIGN PATENT DOCUMENTS 48-98692 12/1973 Japan .
50-122091 9/1975 Japan .
51-124915 10/1976 Japan .
52-107185 9/1977 Japan .
53-59283 5/1978 Japan .

OTHER PUBLICATIONS

Iinuma, K., et al (1976), "High Resolution Linear Electron Scanning Ultrasonic Diagnosis Apparatus"; Japanese Journal of Medical Ultrasonics, vol. 3, No. 4, pp. 13 and 15.

Primary Examiner—John E. Chapman

[57] ABSTRACT

An electronic scanning ultrasonic diagnostic system comprising a probe having ultrasonic beam emitting surface, in which plural ultrasonic wave transducers are convexly arranged at equal distances, emitting desired sector scanning ultrasonic beams, a transmitting and receiving wave control circuit dividing transducers into optional and plural groups and repeatedly performing of transmitting and receiving action with ultrasonic directivities respectively different to each group, and supplying ultrasonic beam scanning signals to an image display section with an assumption that the respective extension lines of each sector scanning ultrasonic beams coincide with the center of the arc shape of the probe.

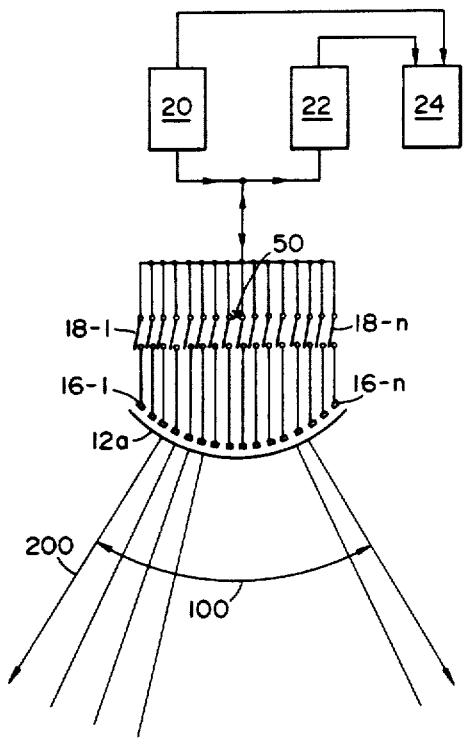

REEXAMINATION CERTIFICATE ISSUED UNDER 35 U.S.C. 307

THE PATENT IS HEREBY AMENDED AS INDICATED BELOW.

Matter enclosed in heavy brackets [] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claims 2-3, dependent on an amended claim, are determined to be patentable.

1. An electronic scanning ultrasonic diagnostic system comprising:
   a probe [havng] *having* ultrasonic beam emitting surface which is pressed to contact the surface of a body to be examined and in which plural ultrasonic wave transducers are convexly arranged at equal distances, said probe emitting desired sector scanning ultrasonic beams into the body without intermediate medium material; and
   means for energizing to drive selected ultrasonic wave [trasducers] *transducers* out of said plural ultrasonic wave transducers according to [the] *a* predetermined *transmitting and receiving timing* program [at every timing of transmitting and receiving waves] *to emit a basic ultrasonic beam directed toward the direction of a center normal line of an arc formed by said selected ultrasonic wave transducers and at least one supplemental beam having a different beam directivity to said basic ultrasonic beam.*

* * * * *